Jan. 20, 1976 W. A. WARRINER Plant Pat. 3,825
ROSE PLANT
Filed April 15, 1974
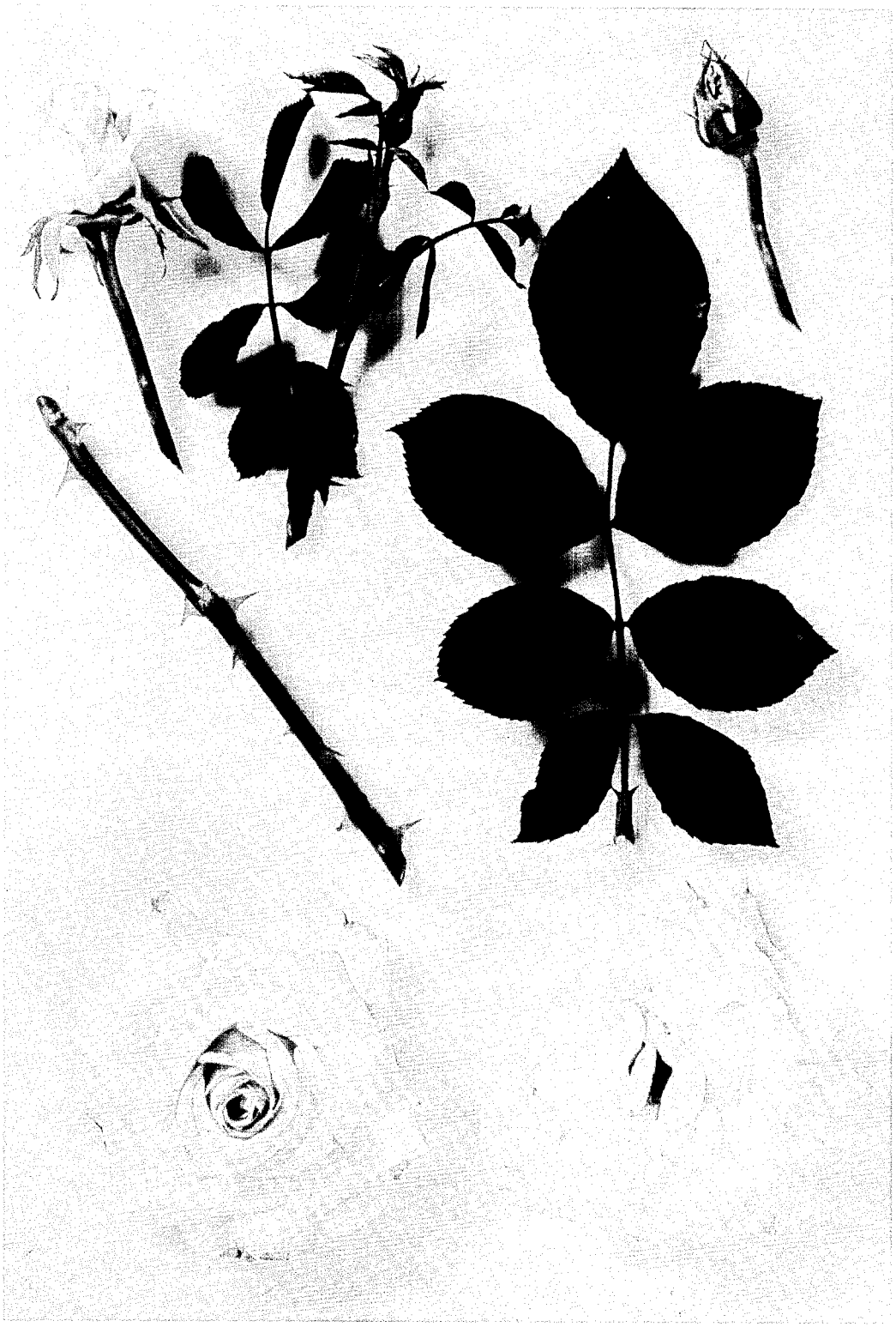

United States Patent

Plant Pat. 3,825

Patented Jan. 20, 1976

3,825

ROSE PLANT

William A. Warriner, 1341 Lurline Lane, Tustin, Calif. 92680

Filed Apr. 15, 1974, Ser. No. 460,691

Int. Cl. A01h *5/00*

U.S. Cl. Plt.—26 1 Claim

The present invention relates to a new and distinct cultivar of rose plant of the floribunda class which was originated by me by crossing an unnamed, unpatented cultivar with pollen from the cultivar, Bridal Pink, U.S. Plant Pat. No. 2,851.

The primary objective of this breeding was to produce a cultivar suitable especially for the production of cut blooms of a pink color similar to the color of Bridal Pink but with improved characteristics of growth and keeping qualities. This objective was fully achieved as evidenced by the following unique combination of characteristics which are outstanding in the new cultivar and which distinguish it from its parents as well as from all other cultivars of which I am aware.

1. Foliage generally larger than that of Bridal Pink and more glossy on the upper side than the leathery (non-glossy) foliage of Bridal Pink.
2. Fewer thorns than Bridal Pink.
3. Very smooth, nearly glossy, surface of stems at the cutting stage of growth.
4. Petal surface is more glossy, or satiny, than Bridal Pink.
5. Flower color of light Carmine Rose (W) with a lighter reverse is similar to Bridal Pink except lighter on the reverse (lower) side of the petals.

Asexual reproduction of this new cultivar by budding as performed at Wasco, California, shows that the described characteristics and distinctions come true to form and are established and transmitted through succeeding propagations.

The accompanying illustration shows typical specimens of the vegetative growth and flowers of the new cultivar in different stages of development, depicted in color as nearly true as it is reasonably possible to make the same in a color illustration of this character.

The following is a detailed description of my new rose variety with color terminology in accordance with *Wilson's Horticultural Color Chart,* except where ordinary dictionary significance of color is indicated.

Parentage: Seedling.
- *Seed Parent.*—Unnamed seedling.
- *Pollen Parent.*—Bridal Pink, U.S. Plant Pat. No. 2,851.

Classification:
- *Botanic.*—Rose hybrid.
- *Commercial.*—Floribunda.

FLOWER

Observations were made at Irvine, Calif, in February from plants grown in a greenhouse.

Blooming habit: Recurrent—continuous.

Bud:
- *Size.*—1¼ inches when petals start to unfurl.
- *Form.*—Pointed ovoid.
- *Color.*—When sepals first divide lighter than Carmine Rose (621/3) with deeper color near outer edges of petals close to Carmine Rose (621). When half bloom; upper side of petals near Carmine Rose (621/1) large area at base of petal near white; lower side of petals lighter than Carmine Rose (621/3) with deeper color near outer edges close to Carmine Rose (621/1).

- *Sepals.*—Color: Outer surface Scheeles Green (860/3). Inner surface Scheeles Green (860/3) with moderate amount of white tomentum. Three appendaged sepals lightly appendaged. Two unappendaged sepals slightly hairy edged.
- *Receptacle.*—Color: Scheeles Green (860/3). Shape: Funnel. Size: Large. Surface: Smooth.
- *Peduncle.*—Length: Medium. Surface: Few stipitate glands. Color: Scheeles Green (860/3). Strength: Stiff, erect, heavy.
- *Opening.*—Spiral type—petal edges curl back slightly.

Bloom:
- *Size.*—Large. Average open size 4½ inches.
- *Borne.*—In greenhouse: Singly and occasionally several together. On plants grown outside, blooms are mostly in clusters.
- *Stems.*—Long.
- *Form.*—When first open—high center. Permanence—retains its form to the end.
- *Petalage.*—Number of petals under normal conditions, 30–35.
- *Color.*—Center of flower: Upper side of petals near Carmine Rose (621/2), large area near base near white with overlay of Primrose Yellow (601/3). Reverse side of petals lighter than upper side, almost white with overcast slightly lighter than Carmine Rose (621/3), slightly deeper near outer edges. Base of petals near white with small area Primrose Yellow (601/3). General tonality from a distance Carmine Rose (621/2). Variegations: None, very smooth color with little or no veination.
- *Discoloration.*—At end of first day—none. Third day—none.
- *Fragrance.*—Very slight.
- *Petals.*—Texture: Thick, satiny.
- *Shape.*—Round, sometimes wider than long.
- *Form.*—Tips slightly recurved.
- *Arrangement.*—Imbricated.
- *Petaloids in center.*—Few.
- *Persistence.*—Drop off cleanly.
- *Lastingness.*—On the plant—very long. As cut flower— very long.

Reproductive parts:
- *Stamens, anthers.*—Medium. Color—yellow. Arrangement—regular around styles.
- *Filaments.*—Color—white.
- *Pollen.*—Gold yellow.
- *Styles.*—Color—base white, tips red.
- *Stigmas.*—Color—light yellow.

PLANT

Form: Bush.

Growth:
- *In greenhouse.*—Vigorous, upright, branching.
- *Outside.*—Low and bushy.

Foliage: Number of leaflets on normal mid-stem leaves, 5–7.
- *Size.*—Very large.
- *Quantity.*—Normal.
- *Color.*—New foliage: Lighter than Garnet Brown (00918/3). Old foliage: Near Parsley Green (00962).

Leaflets:
- *Shape.*—Oval, bluntly pointed.
- *Texture.*—Upper side—glossy.
- *Edge.*—Serrated.
- *Serration.*—Single, small.
- *Petiole (rachis).*—Color—Garnet Brown (00918/3). Underside—prickles.
- *Stipules.*—Medium. Slightly bearded.

*Disease resistance.*—Resistant to mildew under normal growing conditions at Irvine, Calif.

Wood:

*New wood.*—Color—reddish. Bark—smooth.

*Old wood.*—Color—green. Bark—very smooth.

Prickles:

*Quantity.*—On main stalks from base—few. On laterals from stalk—few.

*Form.*—Broad based. Sometimes straight, hooked downwardly.

*Color when young.*—Green.

*Position.*—Irregular.

Small prickles:

*Quantity.*—On main stalks—few to none. On laterals—few to none.

I claim:

1. A new and distinct cultivar of rose plant of the floribunda class, substantially as herein shown and described, characterized particularly as to novelty by the unique combination of its large glossy foliage, relatively fewer thorns than Bridal Pink, smooth stems, glossy petals of light Carmine Rose (W), and productive growth as a cut flower cultivar when grown in a greenhouse.

No references cited.

ROBERT E. BAGWILL, Examiner